(12) United States Patent
Sakuragi (10) Patent No.: US 9,198,603 B2
(45) Date of Patent: Dec. 1, 2015

(54) DEVICE, METHOD AND PROGRAM FOR SEARCHING FOR THE SHORTEST PATH IN A TUBULAR STRUCTURE

(71) Applicant: FUJIFILM Corporation, Tokyo (JP)

(72) Inventor: Futoshi Sakuragi, Tokyo (JP)

(73) Assignee: FUJIFILM CORPORATION, Tokyo (JP)

(*) Notice: Subject to any disclaimer, the term of this patent is extended or adjusted under 35 U.S.C. 154(b) by 121 days.

(21) Appl. No.: 14/033,200

(22) Filed: Sep. 20, 2013

(65) Prior Publication Data

US 2014/0088416 A1    Mar. 27, 2014

(30) Foreign Application Priority Data

Sep. 27, 2012 (JP) ................. 2012-213408

(51) Int. Cl.
| | |
|---|---|
| G06K 9/00 | (2006.01) |
| A61B 5/107 | (2006.01) |
| G06T 19/00 | (2011.01) |
| A61B 5/00 | (2006.01) |
| A61B 5/055 | (2006.01) |
| A61B 5/02 | (2006.01) |
| G06T 7/00 | (2006.01) |
| A61B 6/03 | (2006.01) |

(52) U.S. Cl.
CPC .......... *A61B 5/1075* (2013.01); *A61B 5/0073* (2013.01); *A61B 5/02007* (2013.01); *A61B 5/055* (2013.01); *A61B 5/489* (2013.01); *G06T 7/0083* (2013.01); *G06T 19/00* (2013.01); *A61B 6/032* (2013.01); *G06K 2209/051* (2013.01); *G06T 2207/30048* (2013.01); *G06T 2207/30101* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 8,126,232 B2* | 2/2012 | Dikici et al. | ................... | 382/128 |
| 8,290,228 B2* | 10/2012 | Cohen et al. | ................... | 382/128 |
| 8,463,065 B2* | 6/2013 | Sun et al. | ....................... | 382/260 |
| 8,521,252 B2* | 8/2013 | Diez | .............................. | 600/407 |
| 2003/0063785 A1 | 4/2003 | Oosawa | | |
| 2004/0249270 A1 | 12/2004 | Kondo et al. | | |
| 2008/0267481 A1 | 10/2008 | Nakamura | | |

(Continued)

FOREIGN PATENT DOCUMENTS

| | | |
|---|---|---|
| JP | 11-120327 A | 4/1999 |
| JP | 2002-253539 A | 9/2002 |

(Continued)

OTHER PUBLICATIONS

Kaufhold et al. "Vectorization of optically sectioned brain microvasculature: learning aids completion of vascular graphs by connecting gaps and deleting open-ended segments", Medical Image Analysis, vol. 16, issue 6, Aug. 2012, pp. 1241-1258.*

(Continued)

*Primary Examiner* — Soo Park
(74) *Attorney, Agent, or Firm* — McGinn IP Law PLLC (57) ABSTRACT

A path extraction unit extracts a path of a tubular structure from a three-dimensional image containing the tubular structure, and an interrupted path detection unit detects an interrupted path in the extracted path. A search path generation unit generates a search path that connects the interrupted path, and a search unit searches for the shortest path between a start point and an end point on the extracted path based on the extracted path and the search path.

9 Claims, 4 Drawing Sheets

(56) References Cited

U.S. PATENT DOCUMENTS

| | | | |
|---|---|---|---|
| 2010/0296709 A1* | 11/2010 | Ostrovsky-Berman et al. | 382/128 |
| 2011/0135175 A1* | 6/2011 | Ostrovsky-Berman et al. | 382/128 |
| 2012/0237094 A1 | 9/2012 | Kurihara et al. | |
| 2012/0296620 A1* | 11/2012 | Aulbach | 703/11 |
| 2014/0301618 A1* | 10/2014 | Popovic et al. | 382/128 |

FOREIGN PATENT DOCUMENTS

| | | |
|---|---|---|
| JP | 2004-283373 (A) | 10/2004 |
| JP | 2009-268741 (A) | 11/2009 |

OTHER PUBLICATIONS

Japanese Office Action dated Sep. 8, 2015 with an English translation.

\* cited by examiner

DEVICE, METHOD AND PROGRAM FOR SEARCHING FOR THE SHORTEST PATH IN A TUBULAR STRUCTURE

BACKGROUND OF THE INVENTION

1. Field of the Invention

The present invention relates to a device, a method and a program for extracting a tubular structure, such as a blood vessel, from an image of a subject and searching for the shortest path in the extracted tubular structure.

2. Description of the Related Art

In recent years, along with the advancement of medical equipment (such as a multi-detector CT), high quality three-dimensional images are being used in imaging diagnosis. However, since a three-dimensional image is formed by a number of two-dimensional images and thus has a large volume of information, it may take a long time for a doctor to find a desired site to be observed and diagnose the site. Therefore, an organ of interest is extracted and displayed as a MIP image, a VR image, a CPR image, or the like, to increase visual recognizability of the entire organ and the lesion, thereby increasing the efficiency of the diagnosis.

On the other hand, in order to obtain effective information for diagnosis, such as a CPR image developed along a path of a blood vessel, a site of stenosis and a stenosis rate, when an analysis of cardiac CT images, in particular, an analysis of the coronary arteries or an analysis of the cerebral blood vessels is performed, the center path of the blood vessel, such as the coronary arteries, is extracted as a graph structure from a three-dimensional image containing tubular structures and is displayed. For example, Japanese Unexamined Patent Publication No. 11 (1999)-120327 (hereinafter, Patent Document 1) proposes a technique that involves extracting, from an area between the start point and the target site in a tubular structure, such as a blood vessel, a plurality of center lines running through the center of the tubular structure and leading to the target site, searching for the shortest path from the center lines, and displaying the shortest path superimposed on a displayed image of the corresponding tubular structure.

With the technique disclosed in Patent Document 1, however, the center line may be interrupted at a portion of the blood vessel that is narrowed due to plaque, or the like, or a portion of the tubular structure where a tissue, such as fat, that is different from the tubular structure is deposited. When the center line is interrupted, the shortest path search cannot be achieved. In order to address this problem, a technique that involves receiving a specification of an interrupted portion by the user if the center line is interrupted, and connecting the interrupted portion to enable the shortest path search is proposed (see U.S. Patent Application Publication No. 20040249270 (hereinafter, Patent Document 2)).

SUMMARY OF THE INVENTION

With the technique disclosed in Patent Document 2, however, the user needs to specify the interrupted portion. This makes the operation of confirming the shortest path in the tubular structure complicated and increases the burden imposed on the user who performs the operation.

In view of the above-described circumstances, the present invention is directed to enabling search for the shortest path in a tubular structure from a three-dimensional image without imposing a burden on the user.

An aspect of a device for searching for the shortest path in a tubular structure according to the invention includes: a path extraction unit for extracting a path of a tubular structure from a three-dimensional image containing the tubular structure; an interrupted path detection unit for detecting an interrupted path in the extracted path; a search path generation unit for generating a search path that connects the interrupted path; and a search unit for searching for the shortest path between a start point and an end point on the extracted path based on the extracted path and the search path.

In the device for searching for the shortest path according to the invention, the interrupted path detection unit may detect an area between a terminal point of the extracted path and another part of the extracted path present around the terminal point as being an interrupted path if the distance between the terminal point and the other part of the extracted path is within a predetermined distance.

In the device for searching for the shortest path according to the invention, the interrupted path detection unit may calculate a distance determined by a radius of the tubular structure at a terminal point of the extracted path and a radius of the tubular structure at each of other parts of the extracted path present around the terminal point, and may detect an area between the terminal point and the other part of the extracted path with the shortest distance as being the interrupted path.

The device for searching for the shortest path according to the invention may further include a start and end points setting unit for setting a start point and an end point on the extracted path.

In the device for searching for the shortest path according to the invention, the path extraction unit may correct the extracted path based on an instruction to connect and/or disconnect the extracted path.

In the device for searching for the shortest path according to the invention, the interrupted path detection unit may prohibit detecting a part of the extracted path that is corrected in response to an instruction to disconnect the extracted path as being the interrupted path.

In the device for searching for the shortest path according to the invention, the search unit may search for the shortest path with setting a low priority on the search path.

In the device for searching for the shortest path according to the invention, the path extraction unit may perform a second extraction of the path of the tubular structure at the interrupted path, and the search path generation unit may generate the search path based on a result of the second extraction of the path.

An aspect of a shortest path searching method according to the invention includes the steps of: extracting a path of a tubular structure from a three-dimensional image containing the tubular structure; detecting an interrupted path in the extracted path; generating a search path that connects the interrupted path; and searching for the shortest path between a start point and an end point on the extracted path based on the extracted path and the search path.

It should be noted that the method for searching for the shortest path in a tubular structure according to the invention may be provided in the form of a program for causing the computer to execute the method.

According to the present invention, a path of a tubular structure is extracted from a three-dimensional image containing the tubular structure, an interrupted path in the extracted path is detected, a search path that connects the interrupted path is generated, and the shortest path between a start point and an end point on the extracted path is searched for based on the extracted path and the search path. Therefore, the interrupted path is connected and the shortest path is searched out without any operation by the user. This can reduce the burden imposed on the user during the search of the shortest path in a tubular structure from a three-dimensional image.

Further, in the case where an area between a terminal point of the extracted path and another part of the extracted path present around the terminal point is detected as being an interrupted path when the distance between the terminal point and the other part of the extracted path is within a predetermined distance, a situation where a terminal point that is not a continuous path per se is searched out as a path can be prevented, thereby improving accuracy of the shortest path search.

Also, in the case where a distance determined by a radius of the tubular structure at a terminal point of the extracted path and a radius of the tubular structure at each of other parts of the extracted path present around the terminal point is calculated, and an area between the terminal point and the other part of the extracted path with the shortest distance is detected as being the interrupted path, a situation where an terminal point that is not a continuous path per se is searched out as a path can be prevented, thereby improving accuracy of the shortest path search.

Further, in the case where a start point and an end point on the extracted path are detected, the user does not need to specify the start point and the end point on the path, and the burden imposed on the user can further be reduced.

Further, in the case where an instruction to connect and/or disconnect the extracted path is received, and the path is corrected based on the instruction, the shortest path search can be performed with reflecting the user's intention.

In this case, by prohibiting detecting a part of the extracted path that is corrected in response to an instruction to disconnect the extracted path as being an interrupted path, a situation where a part of the path that is intentionally disconnected by the user is connected by a search path can be prevented.

Further, in the case where the shortest path is searched for with setting a low priority on a search path, a situation where the search path is preferentially searched out as the shortest path does not occur, and this reduces the possibility of searching out an incorrect path.

Further, in the case where the second extraction of the path of the tubular structure from an area between terminal points of an interrupted path is performed, a part of the path that should naturally be present may be searched out. Therefore, by generating a search path based on the result of the second extraction of the path, the shortest path search can be performed using the search path that is more likely to be a part of the path that should naturally be present, thereby improving the accuracy of the shortest path search.

DESCRIPTION OF THE PREFERRED EMBODIMENTS

Figure 1:
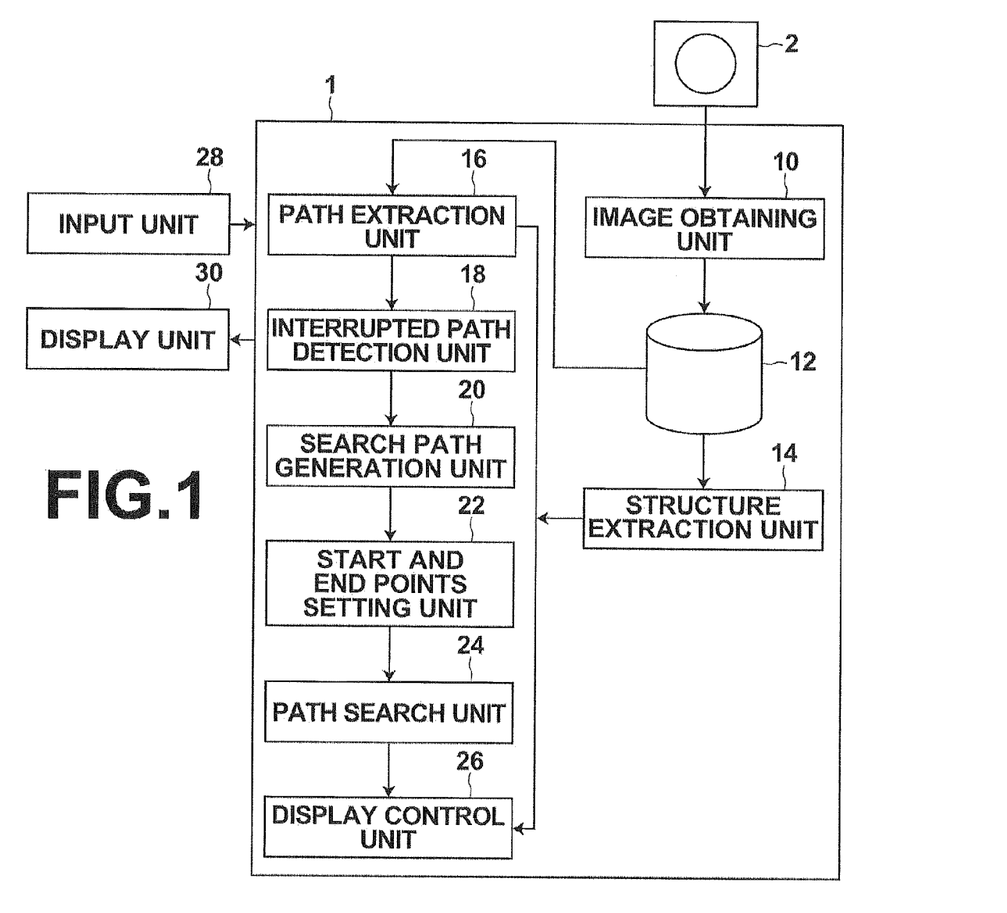
FIG. 1 is a schematic block diagram illustrating the configuration of a three-dimensional image display device, to which a device for searching for the shortest path in a tubular structure according to an embodiment of the present invention is applied.

Hereinafter, an embodiment of the present invention will be described with reference to the drawings. FIG. 1 is a schematic block diagram illustrating the configuration of a three-dimensional image display device, to which a device for searching for the shortest path in a tubular structure according to an embodiment of the invention is applied. It should be noted that the configuration of the three-dimensional image display device 1 shown in FIG. 1 is implemented by executing a three-dimensional image display program, which is read in an auxiliary storage device, on a computer. This program is recorded in a recording medium, such as a CD-ROM, or distributed via a network, such as the Internet, and then is installed on the computer. In the following description, it is assumed that a three-dimensional image is obtained by imaging the chest of a human body, and the tubular structure is the coronary arteries.

The three-dimensional image display device 1 according to this embodiment includes an image obtaining unit 10, a storage unit 12, a structure extraction unit 14, a path extraction unit 16, an interrupted path detection unit 18, a search path generation unit 20, a start and end points setting unit 22, a path search unit 24, a display control unit 26, an input unit 28 and a display unit 30.

The image obtaining unit 10 has a function of a communication interface for obtaining a three-dimensional image V0, which is obtained by imaging the chest of a subject with a modality 2, such as a multislice CT apparatus or a MRI apparatus. In this embodiment, the modality 2 is a multislice CT apparatus. The three-dimensional image V0 is sent from the modality 2 via a LAN.

The three-dimensional image V0 is obtained by stacking two-dimensional tomographic images that are sequentially obtained along the direction perpendicular to slice planes of the chest to be diagnosed. In this embodiment, the three-dimensional image V0 is generated by stacking tomographic images taken with the modality 2. It should be noted that a three-dimensional image obtained by using a CT apparatus is data that stores X-ray absorption levels for individual voxels (i.e., individual pixel positions) forming grid points in a three-dimensional space, where each pixel position is assigned with one signal value (a value indicating the X-ray absorption level in the case where the imaging is performed using a CT apparatus).

It should be noted that, to the three-dimensional image V0, associated information, which is specified by the DICOM (Digital Imaging and Communications in Medicine) standard, is added. The associated information may include, for example, an image ID for identifying each three-dimensional image, a patient ID for identifying each subject, an examination ID for identifying each examination, a unique ID (UID) assigned to each image information, an examination date and time when each image information is generated, a type of modality used in the examination to obtain each image information, patient information, such as name, age, sex, etc., of each patient, examined part (imaged part, the chest in this embodiment), imaging conditions (whether or not a contrast agent is used, radiation dose, etc.), a serial number or a collection number of each image when a plurality of images are obtained in a single examination, etc.

The storage unit 12 is a high capacity storage device, such as a hard disk, and stores the three-dimensional image V0.

The structure extraction unit 14 extracts the heart from the three-dimensional image V0. The extraction of the heart may be achieved by using a technique that involves performing body part recognition, as disclosed, for example, in U.S. Patent Application Publication No. 20080267481, and extracting the heart based on a result of the body part recognition. The technique disclosed in U.S. Patent Application Publication No. 20080267481 involves normalizing inputted tomographic images that forms the three-dimensional image V0, calculating a number of feature quantities from the normalized tomographic images, inputting the feature quantities calculated for each normalized tomographic image to classifiers, which are obtained by using an AdaBoost technique, to calculate, for each body part, a score indicating a likelihood of each tomographic image showing the body part, and determining the body part (i.e., the heart) shown in each tomographic image based on the calculated body part scores by using the dynamic programming method such that the order of the body parts of a human body is maintained. Alternatively, a method using template matching (see, for example, Japanese Unexamined Patent Publication No. 2002-253539) or a method using eigenimages of each body part (i.e., the heart) (see, for example, U.S. Patent Application Publication No. 20030063785) may be used.

The path extraction unit 16 extracts the paths of the coronary arteries in the heart. Specifically, the structure extraction unit 14 calculates eigen values of a 3×3 Hessian matrix for each local area in the extracted heart to search for a line-like structure. In an area that contains a line-like structure, one of three eigen values of the Hessian matrix has a near 0 value and the other two have relatively large values. An eigen vector corresponding to the eigen values having near 0 values indicates the principal axis direction of the line-like structure. Using this relationship, the path extraction unit 16 determines a likelihood of being a line-like structure for each local area based on the eigen values of the Hessian matrix. Then, for each local area that is identified as being a line-like structure, the path extraction unit 16 detects the center point thereof as being a candidate point.

Figure 2:
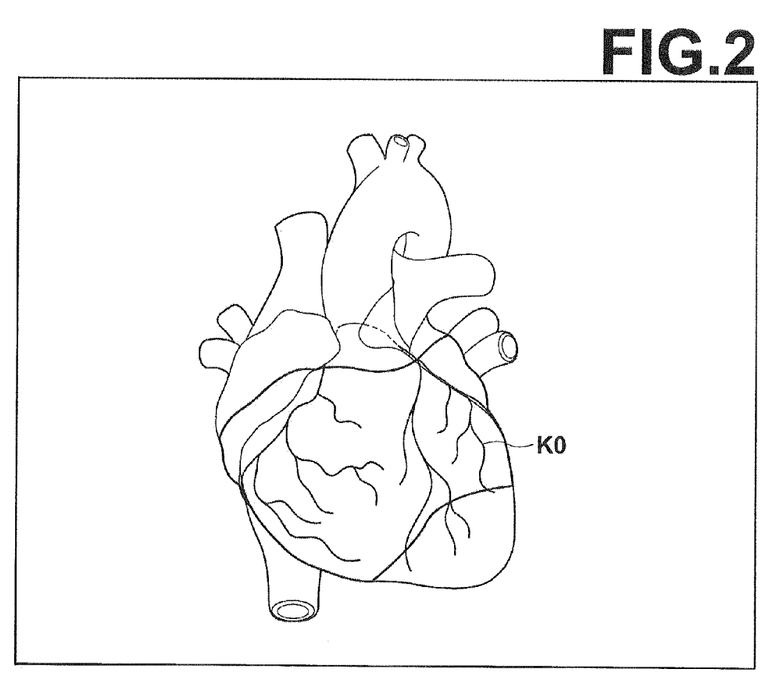
FIG. 2 is a diagram illustrating extracted paths of the coronary arteries.

Then, the candidate points detected by this search are connected based on a predetermined algorithm. In this manner, a tree structure that is formed by blood vessel branches (edges) connecting the candidate points is constructed, and this tree structure is extracted as the paths of the coronary arteries. It should be noted that coordinate information of the candidate points on the path and vector information indicating the directions of the blood vessel branches are stored in the storage unit 12 together with identifiers of the candidate points and the blood vessel branches. Subsequently, for each of the detected candidate points, a contour of the blood vessel (the outer wall of the blood vessel) in a cross-section perpendicular to the path of the coronary artery is identified based on the values (CT values) of voxels around the candidate point. The identification of the shape is achieved by using a known segmentation technique, as typified by Graph-Cuts. Through the above-described operation, a path K0 of the coronary arteries, which are tubular structures, and the coronary arteries are extracted, as shown in FIG. 2. Then, information necessary to identify the extracted path K0 and the coronary arteries are generated and stored in the storage unit 12.

While the path extraction unit 16 extracts the center lines of the coronary arteries as the path, as described above, there may be a case where a part of the path that should naturally be present is interrupted at a portion of the blood vessel that is narrowed due to plaque, or the like, or where a tissue, such as fat, that is different from the blood vessel is deposited. The interrupted path detection unit 18 detects such an interrupted path, which is a part of the path that should naturally be present. To this end, the interrupted path detection unit 18 first detects the terminal point of each branch of the paths extracted by the path extraction unit 16. The detection of the terminal point is achieved by detecting a point where each branch of the path K0 terminates.

Figure 3A:
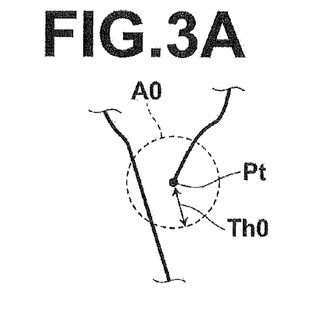
FIG. 3A is a diagram for explaining detection of an interrupted path.
Figure 3B:
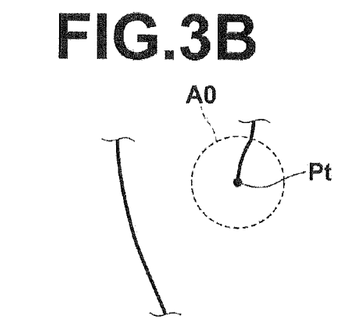
FIG. 3B is a diagram for explaining the detection of an interrupted path.
Figure 3C:
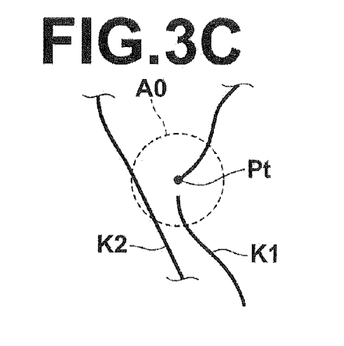
FIG. 3C is a diagram for explaining the detection of an interrupted path.

Then, whether or not another portion of the extracted path K0 is present within a predetermined distance Th0 from the detected terminal point is determined. If it is determined that another part of the extracted path K0 is present, an area between the terminal point and the other part of the extracted path is detected as being an interrupted path. FIGS. 3A to 3C are diagrams for explaining the detection of an interrupted path. As shown in FIG. 3A, the interrupted path detection unit 18 sets a circular area A0 spanning over the predetermined distance Th0 from a terminal point Pt. Then, if another part of the path is present within the circular area A0, an area between the other part of the path and the terminal point Pt is detected as being an interrupted path. In contrast, if no other part of the path is present within the circular area A0, as shown in FIG. 3B, no area is detected as being an interrupted path. Further, in a case where a plurality of parts K1 and K2 of the path are present within the circular area A0, as shown in FIG. 3C, an area between the terminal point Pt and the part K1, which is nearer to the terminal point Pt than the part K2, is detected as being an interrupted path. It should be noted that the predetermined distance Th0 may be set to be an arbitrary value by the user.

Figure 4:
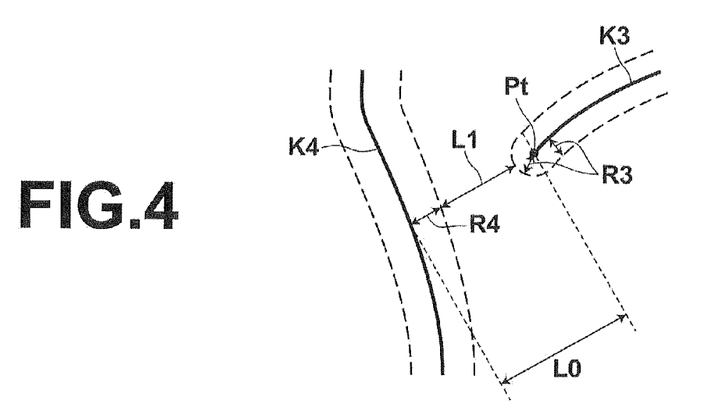
FIG. 4 is another diagram for explaining a detection of an interrupted path.

Instead of the above-described method for detecting an interrupted path, the detection of an interrupted path may be achieved by calculating a distances between a terminal point of the path and each part of the path present around the terminal point, and detecting an area between the terminal point and the part having the shortest distance from the terminal point as being an interrupted path. At this time, the distance between the terminal point and each part of the path present around the terminal point may be determined using a radius of the coronary artery at a position where the branch of the path having the terminal point of interest is extracted and a radius of the coronary artery at a position where each of the other parts of the path, for which the distance is calculated, is extracted. Namely, when a distance between the terminal point Pt of a part K3 and another part K4 of the path, as shown in FIG. 4, is calculated, a distance L1 may be calculated by subtracting a radius R3 of the blood vessel at a position where the part K3 is extracted and a radius R4 of the blood vessel at a position where the part K4 is extracted from a distance L0 between the terminal point Pt and the part K4. Then, an area between the terminal point Pt and the part with the smallest distance L1 may be detected as being an interrupted path. It should be noted that the distance L0 is the shortest distance between the terminal point Pt and the other part K4.

Figure 5:
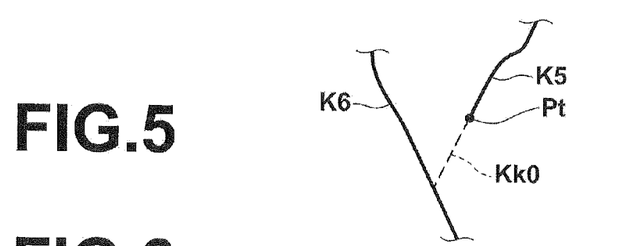
FIG. 5 is a diagram for explaining generation of a search path.

The search path generation unit 20 generates a search path that connects the interrupted path detected by the interrupted path detection unit 18. Namely, as shown in FIG. 5, a search path Kk0 represented by the dashed line is generated between the terminal point Pt of a part K5 of the path and another part K6 that is nearest to the terminal point Pt. At this time, the search path Kk0 is generated to be an extension of the part K5 of the path from the terminal point Pt toward the part K6.

Further, the path extraction unit 16 may perform a second path extraction to extract the path at the interrupted path, i.e., an area between the terminal point Pt and the part K6. In the case where the second path extraction is performed, it may be preferred to improve the accuracy of the extraction by extending a straight line from the terminal point Pt toward the part K6 in smaller increments, by performing the search only in the direction from the terminal point Pt toward the part K6, etc. There is a possibility that a part of the path is extracted with the improved accuracy of the extraction. Then, when a part of the path is extracted, the extracted part of the path may be used as the search path.

Figure 6:
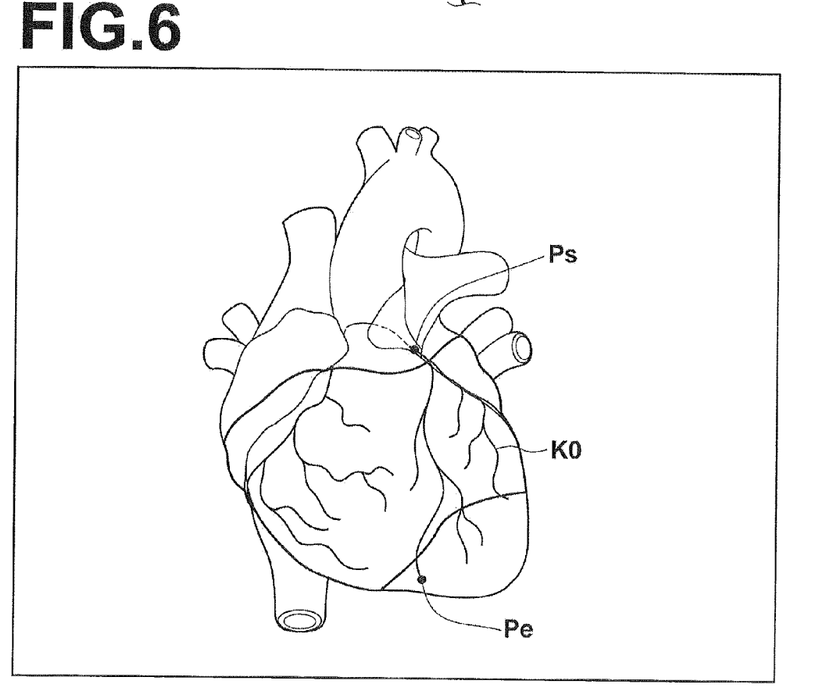
FIG. 6 is a diagram for explaining setting of a start point and an end point.

The start and end points setting unit 22 sets a start point and an end point on the path K0 of the coronary arteries extracted by the path extraction unit 16. Specifically, a volume-rendered image (VR image) of the heart with the path K0 mapped thereon, as shown in FIG. 6, is displayed on the display unit 30 under control of the display control unit 26, and a specification of a start point Ps and an end point Pe made on the VR image by the user via the input unit 28 is received to set the start point Ps and the end point Pe. How the VR image is displayed will be described later. In this embodiment, the start point Ps is a point of connection between the coronary artery and the aorta, and the end point Pe is a distal end of the coronary artery. Alternatively, the start point Ps and the end point Pe may be automatically detected. In this case, the user does not need to specify the start point Ps and the end point Pe on the path, and the burden imposed on the user is reduced.

The path search unit 24 searches for the shortest path between the start point Ps and the end point Pe based on the path extracted by the path extraction unit 16 and the search path(s). Namely, the path search unit 24 performs tracking to detect a length (distance) from the start point Ps to the end point Pe along the path extracted by the path extraction unit 16 and the search path(s). By this tracking, the shortest path from the start point Ps to the end point Pe is detected. Specifically, the shortest path (search vector data of a path with the shortest center line) is detected from different paths for which the length from the start point Ps to the end point Pe is detected, and that path is detected as the shortest path from the start point Ps to the end point Pe.

It should be noted that, when the shortest path is searched for in this manner, a low priority may be set on the search path during the tracking. Specifically, the search path may be weighted such that the length of the search path appears longer than the extracted path of the same length.

Figure 7:
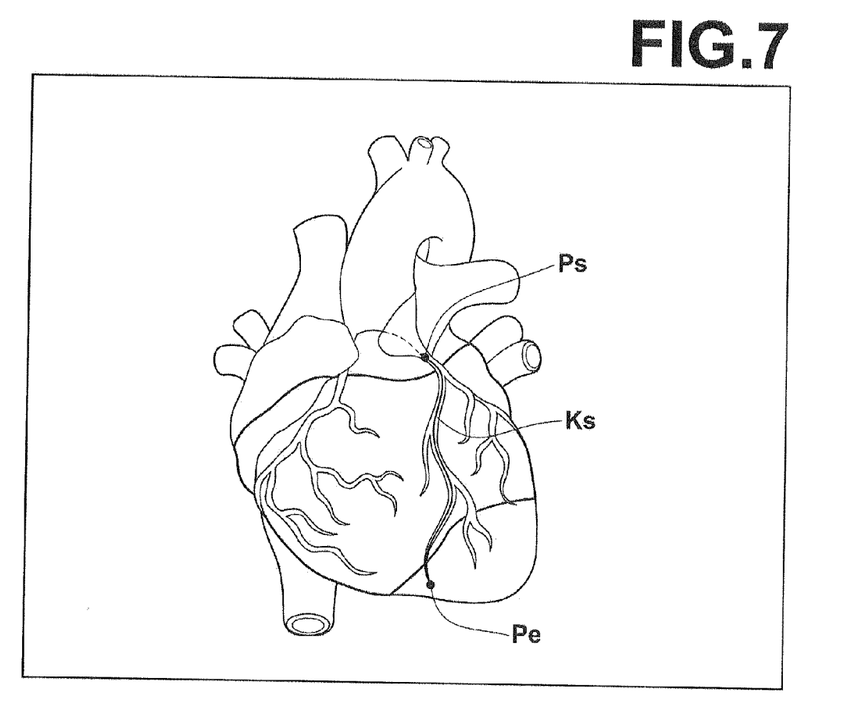
FIG. 7 is a diagram illustrating a VR image with the shortest path mapped thereon.

The display control unit 26 performs volume rendering (VR) display of the heart extracted from the three-dimensional image V0 by the structure extraction unit 14 and the coronary arteries extracted by the path extraction unit 16 using the volume rendering technique. Namely, a virtual light beam is applied to the extracted heart and the coronary arteries from a projection plane to generated a three-dimensional image formed by virtual reflected light from the inside of the objects based on the color (RGB) and opacity corresponding to each signal value of the three-dimensional image V0. From this three-dimensional image, a projection image of a three-dimensional structure inside each object perspectively projected onto the projection plane is generated and is displayed as the VR image. Further, the display control unit 26 displays the shortest path, which is searched out by the path search unit 24, mapped on the coronary arteries. FIG. 7 is a diagram illustrating a VR image with the shortest path mapped thereon. As shown in FIG. 7, a shortest path Ks is mapped on the coronary arteries.

The input unit 28 is formed by a known input device, such as a keyboard and a mouse.

The display unit 30 is formed by a known display device, such as a liquid crystal display or a CRT display.

Figure 8:
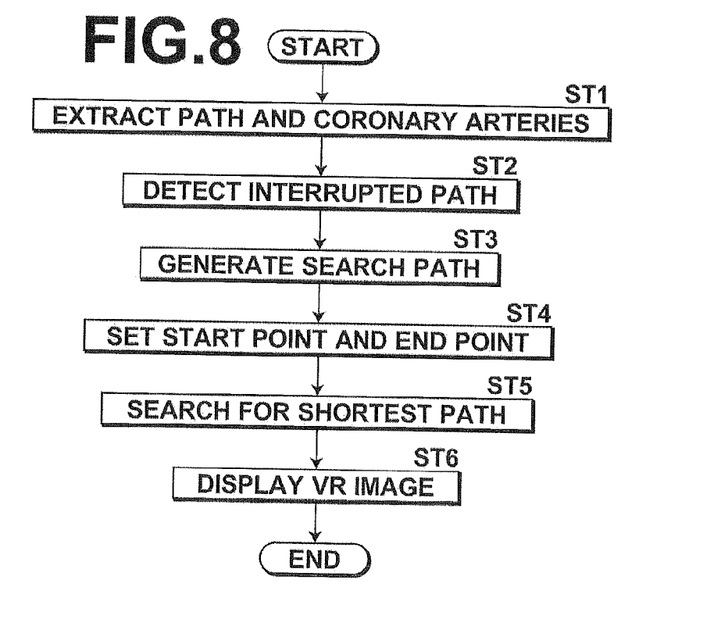
FIG. 8 is a flow chart illustrating a process performed in the embodiment of the invention.

Next, a process performed in this embodiment is described. FIG. 8 is a flow chart illustrating the process performed in this embodiment. It is assumed that the three-dimensional image V0 is obtained by the image obtaining unit 10 and stored in the storage unit 12, and the heart is extracted from the three-dimensional image V0 by the structure extraction unit 14. First, the path extraction unit 16 extracts the paths of the coronary arteries and the coronary arteries (step ST1), and the interrupted path detection unit 18 detects an interrupted path, which is a part of the path that should naturally be present (step ST2).

Then, the search path generation unit 20 generates a search path that connects the interrupted path (step ST3), and the start and end points setting unit 22 sets a start point Ps and an end point Pe on the coronary arteries extracted by the path extraction unit 16 (step ST4). Then, the path search unit 24 searches for the shortest path between the start point Ps and the end point Pe based on the path extracted by the path extraction unit 16 and the search path (step ST5). Further, the display control unit 26 maps the shortest path onto the VR image of the heart and the coronary arteries and displays the VR image with the shortest path mapped thereon on the display unit 30 (step ST6), and the process ends.

As described above, in this embodiment, the paths of the coronary arteries are extracted from the three-dimensional image V0, and an interrupted path in the extracted path is detected. Then, a search path for the interrupted path is generated. Then, the shortest path between the start point Ps and the end point Pe is searched for based on the extracted path and the search path. Therefore, the interrupted path is connected and the shortest path is searched out without any operation by the user. This can reduce the burden imposed on the user during search of the shortest path in a tubular structure, such as the coronary arteries, from the three-dimensional image V0.

Further, since an area between a terminal point of the extracted path and another part of the extracted path present around the terminal point is detected as being an interrupted path when the distance between the terminal point and the other part of the extracted path is within the predetermined distance Th0, a situation where a terminal point that is not a continuous path per se is searched out as a path can be prevented, thereby improving the accuracy of the shortest path search.

Further, since the shortest path search is performed with setting a low priority on the search path, a situation where the search path is preferentially searched out as the shortest path does not occur, and this reduces the possibility of searching out an incorrect path.

Further, in the case where the second extraction of the path is performed at the interrupted path, a part of the path that should naturally be present may be searched out. Therefore, by generating a search path based on the result of the second extraction of the path, the shortest path search can be performed using the search path that is more likely to be a part of the path that should naturally be present, thereby improving the accuracy of the shortest path search.

It should be noted that, although the shortest path is displayed together with the VR image after the shortest path is searched out in the above-described embodiment, the path extraction unit 16 may map the extracted path on the VR image. Then, the VR image with the extracted path mapped thereon may be displayed on the display unit 30, and an instruction to connect and/or disconnect the path by the user may be received via the input unit 28 so that the path extraction unit 16 can correct the extracted path in response to this instruction. This allows performing the shortest path search with reflecting the user's intention. In this case, the user may make an instruction to disconnect the path. Then, it may be prohibited to detect a part of the path that is disconnected according to the instruction by the user as being an interrupted path. This prevents a situation where a part of the path that is intentionally disconnected by the user is connected by a search path.

Further, although the coronary arteries of the heart are used as the tubular structure in the above-described embodiment, this is not intended to limit the invention. The invention is applicable to the shortest path search of a structure having a tubular structure forming a human body, such as the cerebral blood vessels, the bronchial tubes of the lungs, the blood vessels of the liver (the artery, the vein, the portal vein), etc.

What is claimed is:

1. A device for searching for a shortest path in a tubular structure, the device comprising:
    a path extraction unit for extracting a path of a tubular structure from a three-dimensional image containing the tubular structure;
    an interrupted path detection unit for detecting an interrupted path in the extracted path;
    a search path generation unit for generating a search path that connects the interrupted path; and
    a search unit for searching for the shortest path between a start point and an end point on the extracted path based on the extracted path and the search path,
    wherein the interrupted path detection unit calculates a plurality of distances determined by a radius of the tubular structure at a terminal point of the extracted path and a radius of the tubular structure at a plurality of other parts of the extracted path present around the terminal point, and detects an area between the terminal point and the other part of the extracted path with the shortest distance as being the interrupted path.

2. The device for searching for the shortest path as claimed in claim 1, wherein the interrupted path detection unit detects an area between a terminal point of the extracted path and another part of the extracted path present around the terminal point as being an interrupted path if a distance between the terminal point and the other part of the extracted path is within a predetermined distance.

3. The device for searching for the shortest path as claimed in claim 1, further comprising a start and end points setting unit for setting a start point and an end point on the extracted path.

4. The device for searching for the shortest path as claimed in claim 1, wherein the path extraction unit corrects the extracted path based on an instruction to connect and/or disconnect the extracted path.

5. The device for searching for the shortest path as claimed in claim 4, wherein the interrupted path detection unit prohibits detecting a part of the extracted path that is corrected in response to an instruction to disconnect the extracted path as being the interrupted path.

6. The device for searching for the shortest path as claimed in claim 1, wherein the search unit searches for the shortest path with setting a low priority on the search path.

7. The device for searching for the shortest path as claimed in claim 1, wherein the path extraction unit performs a second extraction of the path of the tubular structure at the interrupted path, and
    the search path generation unit generates the search path based on a result of the second extraction of the path.

8. A method for searching for a shortest path in a tubular structure, the method comprising:
    extracting a path of a tubular structure from a three-dimensional image containing the tubular structure;
    detecting an interrupted path in the extracted path;
    generating a search path that connects the interrupted path; and
    searching for the shortest path between a start point and an end point on the extracted path based on the extracted path and the search path,
    wherein said detecting further calculates a plurality of distances determined by a radius of the tubular structure at a terminal point of the extracted path and a radius of the tubular structure at a plurality of other parts of the extracted path present around the terminal point, and detects an area between the terminal point and the other part of the extracted path with the shortest distance as being the interrupted path.

9. A non-transitory computer readable medium containing a program for causing a computer to execute:
    extracting a path of a tubular structure from a three-dimensional image containing the tubular structure;
    detecting an interrupted path in the extracted path;
    generating a search path that connects the interrupted path; and
    searching for the shortest path between a start point and an end point on the extracted path based on the extracted path and the search path,
    wherein said detecting further calculates a plurality of distances determined by a radius of the tubular structure at a terminal point of the extracted path and a radius of the tubular structure at a plurality of other parts of the extracted path present around the terminal point, and detects an area between the terminal point and the other part of the extracted path with the shortest distance as being the interrupted path.

* * * * *